United States Patent
Vats et al.

(10) Patent No.: US 9,750,696 B2
(45) Date of Patent: Sep. 5, 2017

(54) DISSOLUTION ENHANCED CONTROLLED DRUG DELIVERY SYSTEM FOR POORLY WATER SOLUBLE DRUGS

(75) Inventors: Sandeep Kumar Vats, Sonipat (IN); Kalaiselvan Ramaraju, Tiruchirappalli (IN); Romi Barat Singh, Benares (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 14/236,162

(22) PCT Filed: Aug. 1, 2012

(86) PCT No.: PCT/IB2012/053945
§ 371 (c)(1),
(2), (4) Date: Feb. 23, 2015

(87) PCT Pub. No.: WO2013/018050
PCT Pub. Date: Feb. 7, 2013

(65) Prior Publication Data
US 2015/0174071 A1   Jun. 25, 2015

(30) Foreign Application Priority Data
Aug. 1, 2011 (IN) .......................... 2175/DEL/2011

(51) Int. Cl.
| | |
|---|---|
| *A61K 31/41* | (2006.01) |
| *A61K 9/14* | (2006.01) |
| *A61K 9/16* | (2006.01) |
| *A61K 9/20* | (2006.01) |
| *A61K 9/28* | (2006.01) |
| *A61K 9/50* | (2006.01) |
| *A61K 9/48* | (2006.01) |
| *A61K 31/546* | (2006.01) |

(52) U.S. Cl.
CPC ............ *A61K 9/146* (2013.01); *A61K 9/1635* (2013.01); *A61K 9/1641* (2013.01); *A61K 9/2013* (2013.01); *A61K 9/2027* (2013.01); *A61K 9/2031* (2013.01); *A61K 9/2045* (2013.01); *A61K 9/2866* (2013.01); *A61K 9/4808* (2013.01); *A61K 9/5042* (2013.01); *A61K 9/5078* (2013.01); *A61K 31/41* (2013.01); *A61K 31/546* (2013.01); *A61K 9/5047* (2013.01)

(58) Field of Classification Search
CPC ....................................................... A61K 31/41
See application file for complete search history.

(56) References Cited

U.S. PATENT DOCUMENTS

| | | | |
|---|---|---|---|
| 6,706,283 B1 | 3/2004 | Appel et al. ................... | 424/473 |
| 7,364,752 B1 | 4/2008 | Fort et al. ...................... | 424/455 |
| 7,407,670 B2 | 8/2008 | Six et al. ....................... | 424/486 |
| 2003/0157171 A1 | 8/2003 | Chornet et al. ............... | 424/468 |
| 2008/0293828 A1 | 11/2008 | Bouillo et al. ............... | 514/772.3 |
| 2010/0015222 A1* | 1/2010 | Han ..................... | A61K 9/0065 424/468 |

FOREIGN PATENT DOCUMENTS

| | | | |
|---|---|---|---|
| WO | WO 03/024426 | 3/2003 | ............... A61K 9/16 |
| WO | WO 2011/063164 | 5/2011 | ........... A61K 31/353 |
| WO | WO 2011/064111 | 6/2011 | ............. A61K 47/10 |
| WO | WO 2012/058392 | 5/2012 | ............... A61K 9/14 |

OTHER PUBLICATIONS

ExAct (BASF Excipients and Actives for Pharma, No. 23, Oct. 2009).*
BASF, Jul. 2010. *Soluplus—Technical Information* [online] Available from: http://www.pharma-ingredients.basf.com/Statements/Technical%20Informations/EN/Pharma%20Solutions/03_090801e_Soluplus.pdf [Accessed Jan. 10, 2012].

* cited by examiner

*Primary Examiner* — Benjamin Packard

(57) ABSTRACT

The present invention relates to controlled-release pharmaceutical dosage forms comprising a solid dispersion of a poorly water-soluble or insoluble drug with improved solubility and thus improved dissolution in an aqueous medium. The invention further discloses a process of preparation of these controlled-release dosage forms.

14 Claims, No Drawings

DISSOLUTION ENHANCED CONTROLLED DRUG DELIVERY SYSTEM FOR POORLY WATER SOLUBLE DRUGS

FIELD OF THE INVENTION

The present invention relates to controlled-release pharmaceutical dosage forms comprising a solid dispersion of a poorly water-soluble or insoluble drug with improved solubility and thus improved dissolution in an aqueous medium. The invention further discloses a process of preparation of these controlled-release dosage forms.

BACKGROUND OF THE INVENTION

Poorly water-soluble drugs pose many problems when formulated as controlled-release dosage forms. One of the critical problems associated with a poorly water-soluble drug is the very low bioavailability associated with the drug in question. Therefore, directly formulating water-insoluble or poorly soluble drugs into controlled-release systems is likely to lead to failure to achieve the acceptable controlled-release of such drugs. A combination of solubility enhancement and modulating the release is needed to overcome this problem and achieve controlled-release of a water-insoluble or poorly soluble drug.

Several techniques have been developed to enhance the dissolution rate of poorly water-soluble drugs and in turn increase their bioavailability. One such approach involves the use of an amorphous form of the drug. Amorphous materials, however, are thermodynamically unstable and tend to revert to the crystalline form on storage. Another technique is based on particle size reduction, which is intended to increase the contact surface between the drug and the solvent. Size reduction of drugs also causes particle agglomeration due to the static charge. An inadequate control of particle size of the drug can produce variations in the solubilization rate due to agglomeration. Other approaches for increasing the drug dissolution rate of a poorly water-soluble or insoluble drug involve either the incorporation of surfactants/wetting agents or the formation of solid dispersions in water-soluble polymers.

Among these approaches, the formation of solid dispersions is most popular for enhancing the solubility and dissolution. In a solid dispersion, the drug molecules are stabilized in a high-energy state with hydrophilic polymers such as polyethylene glycol, povidone, and polyvinyl alcohol. Solid dispersions can be prepared using various methods such as spray drying and melt-extrusion.

U.S. Pat. No. 7,407,670, assigned to Janssen Pharmaceutica, discloses solid dispersions comprising a first polymer allowing homogeneous or molecular dispersion of a bioactive compound in a matrix and a second polymer enhancing the dissolution of the bioactive compound. U.S. Pat. No. 7,364,752, assigned to Abbott Laboratories, discloses a pharmaceutical composition of ritonavir, wherein ritonavir in the said composition is formulated as a solid dispersion in a matrix including a water-soluble polymer. U.S. Publication No. 2003/0157171 discloses a chitosan-xanthane hydrogel for use as a system capable of modifying the solubilization rates of poorly soluble drugs.

A feature that increases the solubility or dissolution of a poorly soluble drug would generally also increase the rate and extent of absorption of the drug. If such a drug gets eliminated rapidly, it becomes necessary to administer the drug frequently (i.e., several times per day) to maintain uniform blood levels. This is an undesirable situation as frequent dosing is inconvenient for the patient and may lead to noncompliance.

To overcome this problem, it is necessary to include in the pharmaceutical dosage form a first feature to increase solubility or dissolution of the poorly soluble drug and a second feature to slow down and control the rate at which the drug is released from the pharmaceutical dosage form and made available for continuous absorption. The significant benefit that can be achieved is that a dosage regimen with a lower frequency of administration can be designed, thereby resulting in greater patient compliance.

Approaches to resolve this identified problem have been suggested in PCT Publication No. WO 2003/024426. This publication discloses a controlled-release dosage form of carvedilol solid dispersions.

U.S. Pat. No. 6,706,283, assigned to Pfizer, also discloses controlled-release dosage forms for low solubility drugs by coating the core containing the solid dispersion of the drug with a non-dissolving and non-eroding coating that controls the influx of water to the core, i.e., a controlled-release in the form of a reservoir system.

There are a number of polymers which can be used in the preparation of solid dispersion of poorly soluble drugs. Recently, a new polymer Soluplus® has attracted considerable attention for application in preparation of solid dispersions. Soluplus® is a polyvinyl caprolactam-polyvinyl acetate-polyethylene glycol graft copolymer. It has an amphiphilic structure and can be regarded as a polymeric solubilizer. This excipient was commercially launched in 2009 and was designed to be used in hot-melt extrusion and to solubilize poorly soluble drugs. It has an average molecular weight (determined by gel permeation chromatography) which is in the range of 90,000 g/mol to 140,000 g/mol. It is soluble in water, acetone, methanol, ethanol and dimethylformamide. According to the product literature, it is a combination of polyethylene glycol 6000, vinylcaprolactam and vinylacetate. Due to its bifunctional character, it is able to act as a matrix polymer for solid dispersions and also is capable of solubilizing poorly soluble drugs in aqueous media. Furthermore, Soluplus® can also increase the bioavailability of poorly soluble drugs.

There are only a few such references available and there are hardly any commercialized dosage forms based on this concept. Therefore, there is still a need in the art to develop controlled-release pharmaceutical dosage forms for delivery of water-insoluble or poorly soluble drugs that provide improved drug bioavailability and reduced dosing frequency.

It is an object of the present invention to solve these problems associated with water-insoluble or poorly soluble drugs by formulating controlled-release pharmaceutical dosage forms that include solid dispersions of the water-insoluble or poorly soluble drugs.

In the present invention, the inventors have successfully developed a controlled-release system which contains the drug as a solid dispersion prepared by using polyvinyl caprolactam-polyvinyl acetate-polyethylene glycol graft copolymer as a carrier, which is summarized and described in detail below.

SUMMARY OF THE INVENTION

In one general aspect, there is provided a controlled-release pharmaceutical dosage form of a poorly water-soluble or insoluble drug comprising the solid dispersion of said drug, one or more of controlled-release material, and one or more of pharmaceutically acceptable excipients wherein the said solid dispersion comprises the said drug dispersed in polyvinyl caprolactam-polyvinyl acetate-polyethylene glycol graft copolymer.

Embodiments of the above aspect may include one or more of the following features. For example, the controlled-release pharmaceutical dosage form may be a matrix-type dosage form or a reservoir-type dosage form and may be in the form of hard or soft gelatin capsules, tablets, capsules, caplets, pills, granules or mini-tablets.

The controlled-release material may comprise hydrophilic polymers, hydrophobic polymers, water-swellable polymers, hydrophobic materials, or mixtures thereof. The amount of the controlled-release material may comprise from about 2% to about 95% by weight of the dosage form.

The drug to polyvinyl caprolactam-polyvinyl acetate-polyethylene glycol graft copolymer ratio weight by weight may vary from 1:1 to 1:5.

The pharmaceutically acceptable excipients may comprise one or more of binders, fillers/diluents, disintegrants, anti-adherents, lubricants/glidants, plasticizers, coloring agents and flavoring agents.

In another general aspect, there is provided a process for the preparation of a controlled-release pharmaceutical dosage form of a poorly water-soluble or insoluble drug comprising the solid dispersion of said drug, one or more of controlled-release material, and one or more of pharmaceutically acceptable excipients wherein the said solid dispersion comprises said drug dispersed in polyvinyl caprolactam-polyvinyl acetate-polyethylene glycol graft copolymer and wherein the process includes combining the solid dispersion, the controlled-release material, and pharmaceutically acceptable excipient and processing into the dosage form using appropriate toolings.

The details of various embodiments of the invention are set forth in the description below. Other features and advantages of the invention will also be apparent from the description.

DETAILED DESCRIPTION OF THE INVENTION

The preferred classes of drugs that may be included in the dosage forms of the invention are, but not limited to, antihypertensives, antianxiety agents, antidepressants, barbiturates, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, antiobesity agents, autoimmune disorders agents, anti-impotence agents, antibacterial and antifungal agents, hypnotic agents, anti-Parkinsonism agents, anti-Alzheimer's disease agents, antibiotics and antiviral agents.

Specific examples of the above and other classes of drugs and therapeutic agents deliverable by the invention are set forth below, by way of example only. Specific examples of antihypertensives include prazosin, nifedipine, trimazosin, valsartan and doxazosin; a specific example of a blood glucose-lowering agent is glipizide; a specific example of an anti-impotence agent is sildenafil citrate; specific examples of antineoplastics include chlorambucil, lomustine and echinomycin; a specific example of an imidazole-type antineoplastic is tubulazole; specific examples of anti-inflammatory agents include betamethasone, prednisolone, aspirin and flurbiprofen; a specific example of a barbiturate is phenobarbital; specific examples of antivirals include acyclovir and virazole; specific examples of vitamins/nutritional agents include retinol and vitamin E; specific examples of beta blockers include carvedilol, timolol and nadolol; a specific example of an emetic is apomorphine; specific examples of diuretics include chlorthalidone and spironolactone; a specific example of an anticoagulant is dicumarol; specific examples of cardiotonics include digoxin and digitoxin; specific examples of androgens include 17-methyltestosterone and testosterone; a specific example of a steroidal hypnotic/anesthetic is alfaxalone; specific examples of anabolic agents include fluoxymesterone and methanstenolone; specific examples of antidepression agents include sulpiride, fluoxetine, paroxetine, venlafaxine, and sertraline; specific examples of antibiotics include cefpodoxime proxetil, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole and griseofulvin; specific examples of anthelmintic agents include thiabendazole and oxfendazole; specific examples of antihistamines include astemizole, levocabastine, cetirizine and cinnarizine; specific examples of antipsychotics include fluspirilene, penfluridole and ziprasidone; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid and lisinopril; specific examples of tetracycline antibiotics include tetracycline and minocycline; specific examples of macrolide antibiotics include azithromycin, clarithromycin, erythromycin and spiramycin.

Still further examples of drugs deliverable by the invention are the glucose-lowering drug chlorpropamide, the anti-fungal fluconazole, the anti-hypercholesterolemic atorvastatin calcium, the antipsychotic thiothixene hydrochloride, the anxiolytics hydroxyzine hydrochloride and doxepin hydrochloride, the anti-hypertensive amlodipine besylate, the anti-inflammatories iroxicam, valdecoxib and celicoxib, and the antibiotics carbenicillin indanyl sodium, becampicillin hydrochloride, troleandomycin and doxycycline hyclate.

The term "controlled-release", as used herein, includes matrix-type controlled-release pharmaceutical dosage form, reservoir-type controlled-release pharmaceutical dosage form, or combinations of both. The matrix-type dosage forms are those in which the drug is distributed uniformly in one or more of controlled-release materials and reservoir-type compositions utilize polymeric coating over a core comprising the drug. A combination of the reservoir and matrix types includes controlled-release coatings on controlled-release matrices.

The controlled-release materials as used in the dosage form may comprise hydrophilic polymers, hydrophobic polymers, water-swellable polymers, hydrophobic material, and mixtures thereof. The controlled-release material may comprise from about 2% to about 95% by weight of the composition.

Examples of hydrophilic polymers include, but are not limited to, cellulose derivatives, alginates, polyvinyl alcohol, povidone, carbomer, xanthan gum, guar gum, locust bean gum, potassium pectate, potassium pectinate, polyvinylpyrrolidone, polysaccharide, polyalkylene oxides, polyalkyleneglycol, starch and derivatives, and mixtures thereof.

Examples of hydrophobic polymers include, but are not limited to, ethyl cellulose, hydroxyethylcellulose, cellulose acetate, cellulose acetate butyrate, cellulose acetate phthalate, cellulose acetate trimellitate, hydroxypropyl methylcellulose phthalate, poly (alkyl) methacrylate, and copolymers of acrylic or methacrylic acid esters, polyvinyl acetate, and mixtures thereof.

Examples of water-swellable polymers include, but are not limited to, polyethylene oxide; poly(hydroxy alkyl methacrylate); poly(vinyl) alcohol; a mixture of methyl cellulose, cross-linked agar and carboxymethyl cellulose; Carbopol® carbomer; Cyanamer® polyacrylamides; cross-linked water swellable indene-maleic anhydride polymers; Goodrich® polyacrylic acid; starch graft copolymers; Aqua Keep's® acrylate polymer polysaccharides; Amberlite® ion exchange resins; Explotab® sodium starch glycolate; and Ac-Di-Sol® croscarmellose sodium.

Examples of hydrophobic materials include, but are not limited to, waxes, fatty acids, fatty alcohols, fatty acid esters, vegetable oil and mineral oil.

The term "solid dispersion", as used herein, includes a solution or dispersion of the drug in a polymer such as Soluplus® in a solid state. The solid dispersion improves the solubility and bioavailability of the drug. In a solid dispersion the drug attains a high-energy state, thus rendering the drug more soluble by facilitating the solvent action for dissolution to occur. Hence, when administered, the drug is released into the gastrointestinal tract in a highly dispersed form and there is a manifold increase in the effective surface area available for dissolution. The drug to polymer ratio w/w may vary from 1:1 to 1:5.

Prior to formation of the dispersion the drug in its pure state may be crystalline or amorphous, but when dispersed in the solid dispersion polymer a major portion of the drug is preferably in an amorphous or non-crystalline state.

By "amorphous state", it is meant that the drug may be present in the dispersion in any of three broad classes of forms: (a) in discrete, drug-rich domains; (b) homogeneously distributed therein, i.e., a solid dispersion; or (c) any state or combination of states between the extremes of (a) and (b).

The solid dispersion preparation may include a process including dispersing the drug in a polymer using one or more of mechanical mixing, hot-melt, co-melt and congealing, and solvent evaporation techniques.

Preparation of a solid dispersion by mechanical mixing includes vigorous mixing, grinding or trituration of the drug and carrier by any means including use of ball milling, hammer mill or air-jet mill.

Preparation of the solid dispersion by co-melting and hot-melt extrusion includes direct heating of the physical mixture of the drug and the polymer until the mixture has melted, followed by cooling and solidification under rigorous stirring. The final solid mass may further be crushed, pulverized, and sieved.

In the solvent evaporation method, a homogeneous solution of drug and the polymer is prepared in a solvent, alone or along with other excipients that may or may not be dissolved, followed by solvent removal by precipitation or evaporation. Precipitation is typically induced by contacting the drug/dispersion polymer solution with a non-solvent such as water, a liquid hydrocarbon or super-critical $CO_2$. A preferred method of forming the dispersion is by dissolving the drug and the polymer in a common solvent, then removing the solvent by spray-drying the solution. Solvents may include, but are not limited to, water, ethanol, isopropyl alcohol, acetone, chloroform, methanol, methylethylketone, methylene chloride, tertiary butanol, or combination thereof.

The terms "spray-drying" and "spray-coating" in connection with the present invention are used conventionally, and broadly refer to processes involving breaking up liquid mixtures into small droplets (atomization) and rapidly removing a solvent from the mixtures in a vessel such as a spray-drying apparatus or a fluidized bed or pan-coater where there is a strong driving force for evaporation of the solvent from the droplets. In the case of spray-coating, the droplets impinge on a particle, bead, pill, tablet, or capsule, resulting in a coating comprising the solid amorphous dispersion.

There are a number of polymers which may be combined with Soluplus® used in the preparation of solid dispersion of poorly soluble drugs. The most commonly used are polyethylene glycols, polyvinyl pyrrolidone, lactose, cyclodextrins and hydroxypropyl methylcellulose. Surfactants such as polyethylene-polypropylene glycol (Poloxamer) have also been used for this purpose. Solid dispersions with Soluplus® can be formulated into solid dosage forms, e.g., hard gelatin capsules, compressed into tablets and layered on an inert core. The poorly soluble drug and Soluplus® need to be first dissolved in an appropriate solvent. This solution then can be sprayed onto inert pellets (nonpareils).

In addition, a surfactant may also be included in the solid dispersion. Surfactants may include both non-ionic and ionic (cationic, anionic and zwitter-ionic) surfactants suitable for use in pharmaceutical dosage forms. These include polyethoxylated fatty acids and their derivatives, for example, polyethylene glycol 400 distearate, polyethylene glycol-20 dioleate, polyethylene glycol 4-150 mono dilaurate, and polyethylene glycol-20 glyceryl stearate; alcohol-oil transesterification products, for example, polyethylene glycol-6 corn oil; polyglycerized fatty acids, for example, polyglyceryl-6 pentaoleate; propylene glycol I fatty acid esters, for example, propylene glycol monocaprylate; mono and diglycerides, for example, glyceryl ricinoleate; sterol and sterol derivatives; sorbitan fatty acid esters and its derivatives, for example, polyethylene glycol-20 sorbitan monooleate and sorbitan monolaurate; polyethylene glycol alkyl ether or phenols, for example, polyethylene glycol-20 cetyl ether and polyethylene glycol-10-100 nonyl phenol; sugar esters, for example, sucrose monopalmitate; polyoxyethylene-polyoxypropylene block copolymers known as poloxamer; ionic surfactants, for example sodium caproate, sodium glycocholate, soy lecithin, sodium stearyl fumarate, propylene glycol alginate, octyl sulfosuccinate disodium, and palmitoyl carnitine.

In addition, the dosage form further includes pharmaceutically acceptable excipients. For example, one or more pharmaceutically acceptable excipients such as binders, fillers/diluents, disintegrants, anti-adherents, lubricants/glidants, plasticizers, coloring agents and flavoring agents.

Suitable examples of binders include, but are not limited to, acacia, sodium alginate, starch, gelatin, saccharides (including glucose, sucrose, dextrose and lactose), molasses, extract of Irish moss, panwar gum, ghatti gum, mucilage of isapol husk, carboxymethylcellulose, methylcellulose, veegum, larch arabolactan, polyethylene glycols, ethylcellulose, water, alcohols, waxes, polyvinylpyrrolidone such as PVP K90, or mixtures thereof.

Suitable examples of fillers/diluents include, but are not limited to, dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol, or mixtures thereof.

Suitable examples of disintegrants include, but are not limited to, starches, clays, cellulose derivatives including crosscarmellose, gums, algins, various combinations of hydrogencarbonates with weak acids (e.g., sodium hydrogencarbonate/tartaric acid or citric acid) crosprovidone, sodium starch glycolate, agar, cation exchange resins, citrus pulp, veegum HV, natural sponge, bentonite, or mixtures thereof.

Suitable examples of lubricants/glidants include, but are not limited to, talc, magnesium stearate, calcium stearate, steeric acid, hydrogenated vegetable oils, sodium benzoate, sodium chloride, leucine, carbowax 4000, magnesium lauryl sulfate, colloidal silicon dioxide, and mixtures thereof.

Suitable examples of plasticizers include, but are not limited to, phosphate esters; phthalate esters; mineral oils; fatty acids and esters; fatty alcohols, vegetable oils and hydrogenated vegetable oils including acetylated hydrogenated cottonseed glyceride and acetylated hydrogenated soybean oil glycerides; acetyl tributyl citrate; acetyl triethyl citrate; Castor oil; diacetylated monoglycerides; dipropylene glycol salicylate glycerin; glyceryl cocoate; mono- and di-acetylated monoglycerides; phthalyl glycolate; diocyl phthalate; sorbitol, sorbitol glyceryl tricitrate; sucrose octaacetate; a-tocopheryl; polyethylene glycol succinate; phosphate esters; phthalate esters; amides; mineral oils; fatty acids and esters; fatty alcohols including cetostearyl alcohol, cetyl alcohol, stearyl alcohol, oleyl alcohol and myristyl alcohol; methyl abietate; acetyl tributyl citrate; acetyl triethyl citrate; diisooctyl adipate; amyl oleate; butyl ricinoleate; benzyl benzoate; butyl and glycol esters of fatty acids; butyl diglycol carbonate; butyl oleate; butyl stearate; di(beta-methoxyethyl) adipate; dibutyl sebacate; dibutyl tartrate; diisobutyl adipate; dihexyl adipate; triethylene glycol; di(beta-ethyl butyrate); polyethylene glycol; diethylene glycol monolaurate; monomeric polyethylene ester; hydrogenated methyl ester of rosin; methoxyethyl oleate; butoxyethyl stearate; butyl phthalyl butyl glycolate; glycerol tributyrate; and triethylene glycol.

Suitable examples of coloring agents include, but are not limited to, water-soluble FD&C dyes and mixtures thereof with corresponding lakes and direct compression sugars such as Di-Pac from Amstar. In addition, colored dye migration inhibitors such as tragacanth, acacia or attapulgite talc may be added. Specific examples include calcium carbonate, chromium-cobalt-aluminium oxide, ferric ferrocyanide, ferric oxide, iron ammonium citrate, iron (III) oxide hydrated, iron oxides, magnesium carbonate, and titanium dioxide.

The controlled-release dosage forms according to the present invention may take the form of tablets, which may be produced by compressing the final mix of granules and/or powders into tablets. Alternatively, controlled-release dosage forms according to the present invention may take the form of pellets which are coated with the solid dispersion of drug followed by the controlled-release coating. The coating of the pellets may be carried out in the Wurster coating system or in any other conventional coating system. The final pellets may be filled into capsules or compressed into tablets.

In addition, the controlled-release pharmaceutical dosage form can optionally have one or more coatings, which are functional or non-functional.

Suitable examples of polymers useful for coating include, but are not limited to, cellulose acetate, ethyl cellulose, polyamide, polyethylene, polyethylene tereppthalate, polypropylenem polyurethane, polyvinyl acetate, polyvinyl chloride, polyhydroxybutyrate, polyhydroxyvalerate, polylactic acid or polyglycolic acid and copolymers thereof, copolymers such as ethylene vinyl acetate (EVA), styrene-butadienestyrene (SBS) and styrene-isoprene-styrene (SIS).

The controlled-release pharmaceutical dosage form may be prepared by one of more of the following processes:

A suitable process of preparation of the dosage form includes the following steps:

1. melting the physical mixture of the drug and polyvinyl caprolactam-polyvinyl acetate-polyethylene glycol graft copolymer and optionally other pharmaceutically acceptable excipients under continuous and rigorous stirring;
2. cooling the melted mixture with continuous and rigorous stirring and optionally using the melted mixture as granulating fluid;
3. crushing or sifting the final solid mass obtained in step 2 and mixing with other pharmaceutically acceptable excipients;
4. processing the final blend obtained in step 3 into dosage forms using appropriate toolings; and
5. coating the final dosage form obtained in step 4 with the controlled-release materials and optionally other pharmaceutically acceptable excipients using appropriate toolings.

Another suitable process of preparation of the dosage form includes the following steps:

1. extruding the physical mixture of the drug and polyvinyl caprolactam-polyvinyl acetate-polyethylene glycol graft copolymer and optionally other pharmaceutically acceptable excipients using a hot-melt extruder;
2. spheronizing the extrudes in a merumeriser;
3. coating the pellets of step 2 using a controlled-release material and optionally other pharmaceutically acceptable excipients; and
4. filling the pellets into capsules or compressing them into tablets using appropriate toolings.

Another suitable process of preparation of the dosage form includes the following steps:

1. dissolving the physical mixture of the drug and polyvinyl caprolactam-polyvinyl acetate-polyethylene glycol graft copolymer and optionally other pharmaceutically acceptable excipients under continuous and rigorous stirring in a common solvent;
2. evaporating the solvent, crushing or sifting the final solid mass and mixing with other pharmaceutically acceptable excipients;
3. processing the final blend obtained in step 2 into a dosage form using appropriate toolings; and
4. coating the final dosage form obtained in step 3 with the controlled-release materials and optionally other pharmaceutically acceptable excipients using appropriate tooling.

Another suitable process of preparation of the dosage form includes the following steps:

1. dissolving the physical mixture of the drug and polyvinyl caprolactam-polyvinyl acetate-polyethylene glycol graft copolymer and optionally other pharmaceutically acceptable excipients under continuous and rigorous stirring in a common solvent;
2. loading sugar spheres in the Wurster system and coating the sugar spheres with the dispersion of step 1 to form pellets;
3. coating the drug layered pellets obtained in step 2 with the controlled release materials and optionally other pharmaceutically acceptable excipients using appropriate tooling; and
4. filling the pellets into capsules or compressing them into tablets using appropriate tooling.

The invention is further illustrated by the following examples, which are for illustrative purposes only and should not be construed as limiting the scope of the invention in any way.

EXAMPLES

Example 1

Melt Adsorbed Reservoir System

| Ingredient | % w/w of tablet |
|---|---|
| Core | |
| Valsartan | 37.78 |
| Soluplus ® | 37.78 |
| Microcrystalline cellulose | 14.16 |
| Talc | 1.18 |
| Coating | |
| Ethyl cellulose | 7.27 |
| Polyvinyl pyrrolidone (PVP K-30) | 1.81 |
| Isopropyl alcohol | qs |
| Water | qs |

Procedure:
1. Valsartan and Soluplus® were melted in a container under continuous stirring.
2. Microcrystalline cellulose was taken into a Rapid Mixer Granulator and granulated with the molten liquid of step 1 and cooled at room temperature.
3. The cooled granules were sifted using a sieve of size number BSS#30.
4. The granules of step 3 were lubricated with talc and compressed into tablets with a suitable tooling.
5. Ethyl cellulose and polyvinyl pyrrolidone (PVP K-30) were dissolved in an isopropyl alcohol and water mixture.
6. The solution of step 5 was used to coat the tablets obtained in step 4.

Example 2

Melt Adsorbed Reservoir System

| Ingredient | % w/w of tablet |
|---|---|
| Core | |
| Cefpodoxime Proxetil | 26.86 |
| Soluplus ® | 42.97 |
| Microcrystalline cellulose | 20.14 |
| Talc | 1.34 |
| Coating | |
| Cellulose acetate | 8.21 |
| Polyethylene glycol (PEG 600) | 0.45 |
| Triacetin | 0.45 |
| Acetone | qs |
| Water | qs |

Procedure:
1. Cefpodoxime Proxetil and Soluplus® were melted in a container under continuous stirring.
2. Microcrystalline cellulose was taken into a Rapid Mixer Granulator and granulated with the molten liquid of step 1 and cooled at room temperature.
3. The cooled granules were sifted using a sieve of size number BSS#30.
4. The granules of step 3 were lubricated with talc and compressed into tablets with a suitable tooling.
5. Cellulose acetate, polyethylene glycol (PEG 600) and triacetin were dissolved in an acetone and water mixture.
6. The solution of step 5 was used to coat the tablets obtained in step 4.

Example 3

Inert Core Loaded Reservoir System

| Ingredient | % w/w of tablet |
|---|---|
| Core | |
| Carvedilol | 14.54 |
| Soluplus ® | 54.54 |
| Sugar spheres (size BSS#35-40) | 21.81 |
| Acetone | qs |
| Water | qs |
| Coating | |
| Ethyl cellulose | 7.27 |
| Hydroxypropyl methyl cellulose (HPMC 5 cps) | 1.36 |
| Acetyl tributyl citrate | 0.45 |
| Isopropyl alcohol | qs |
| Water | qs |

Procedure:
1. Carvedilol and Soluplus® were dissolved in an acetone and water mixture.
2. Sugar spheres were loaded in the Wurster coating system and coated with the solution of step 1.
3. Ethyl cellulose, hydroxypropyl methyl cellulose (HPMC 5 cps) and acetyl tributyl citrate were dissolved in an isopropyl alcohol and water mixture.
4. The drug layered pellets were further coated with the solution of step 3.
5. The coated pellets were filled into capsules.

Example 4

Solid Dispersion in Lipidic Polymer

| Ingredient | % w/w of tablet |
|---|---|
| Core | |
| Valsartan | 36.36 |
| Soluplus ® | 36.36 |
| Glyceryl behenate | 22.72 |
| Aerosil 200 | 2.27 |
| Magnesium stearate | 2.27 |
| Isopropyl alcohol | qs |

Procedure:
1. Valsartan and Soluplus® were melted in a container under slow stirring and cooled immediately using liquid nitrogen.
2. The molten solid dispersion of step 1 was milled and sifted using appropriate sieves.
3. The solid dispersion of step 2 was mixed with glyceryl behenate and granulated using isopropyl alcohol.
4. The granules were dried and lubricated with an Aerosil 200 and magnesium stearate mixture and compressed into tablets using suitable tooling.

Example 5

Hot Melt Extruded Reservoir System

| Ingredient | % w/w of tablet |
|---|---|
| Core | |
| Carvedilol phosphate | 11.9 |
| Soluplus ® | 35.71 |
| Coating | |
| Cellulose acetate | 47.14 |
| Polyethylene glycol (PEG 6000) | 2.61 |
| Triacetin | 2.61 |
| Acetone | qs |
| Water | qs |

Procedure:
1. Carvedilol phosphate and Soluplus® were put into a hot-melt extruder and extruded.
2. The extrudes were spheronized in a merumeriser to form pellets.
3. Pellets obtained from step 2 were coated using cellulose acetate-polyethylene glycol (PEG 6000)-triacetin solution in an acetone and water mixture.
4. The Coated pellets were filled into suitable capsules.

We claim:

1. A controlled-release pharmaceutical dosage form of a poorly water-soluble or insoluble drug comprising the solid dispersion of said drug, one or more of controlled-release material to slow the release of the drug, and one or more of pharmaceutically acceptable excipients; wherein the said solid dispersion comprises the said drug dispersed in polyvinyl caprolactam-polyvinyl acetate-polyethylene glycol graft copolymer in a ratio of drug to graft copolymer at a weight by weight ratio of from 1:1 to 1:5.

2. The controlled-release pharmaceutical dosage form of claim 1, wherein the dosage form is a matrix-type dosage form or a reservoir-type dosage form.

3. The controlled-release pharmaceutical dosage form of claim 1, wherein the dosage form is in the form of hard or soft gelatin capsules, tablets, capsules, caplets, pills, granules or mini-tablets.

4. The controlled-release pharmaceutical dosage form of claim 1, wherein the controlled-release material comprises hydrophilic polymers, hydrophobic polymers, water-swellable polymers, hydrophobic materials, or mixtures thereof.

5. The controlled-release pharmaceutical dosage form of claim 4, wherein the amount of the controlled-release material comprises from about 2% to about 95% by weight of the dosage form.

6. The controlled-release pharmaceutical dosage form of claim 1, wherein the pharmaceutically acceptable excipients comprise one or more of binders, fillers/diluents, disintegrants, anti-adherents, lubricants/glidants, plasticizers, coloring agents and flavoring agents.

7. A process for the preparation of a controlled-release pharmaceutical dosage form of a poorly water-soluble or insoluble drug comprising the solid dispersion of said drug, one or more of controlled-release material to slow the release of the drug, and one or more of pharmaceutically acceptable excipients; wherein the said solid dispersion comprises said drug dispersed in polyvinyl caprolactam-polyvinyl acetate-polyethylene glycol graft copolymer in a ratio of drug to graft copolymer at a weight by weight ratio of from 1:1 to 1:5; and wherein the process includes combining the solid dispersion, the controlled-release material and pharmaceutically acceptable excipient and processing into the dosage form using appropriate toolings.

8. The controlled-release pharmaceutical dosage form of claim 1, wherein the controlled-release material slows the release of the drug to provide for release in a continuous manner.

9. The controlled-release pharmaceutical dosage form of claim 8, wherein the controlled-release material releases the drug to provide for absorption in a continuous manner.

10. The controlled-release pharmaceutical dosage form of claim 7, wherein the controlled-release material slows the release of the drug to provide for release in a continuous manner.

11. The controlled-release pharmaceutical dosage form of claim 10, wherein the controlled-release material releases the drug to provide for absorption in a continuous manner.

12. The controlled-release pharmaceutical dosage form of claim 2, wherein the dosage form is a reservoir-type dosage form comprising a core and a controlled release coating, and the core comprises the drug and polyvinyl caprolactam-polyvinyl acetate-polyethylene glycol graft copolymer.

13. The controlled-release pharmaceutical dosage form of claim 12, wherein the controlled release coating comprises a polymer.

14. The controlled-release pharmaceutical dosage form of claim 13, wherein the polymer comprises one or more of cellulose acetate, ethyl cellulose, polyamide, polyethylene, polyethylene terephthalate, polypropylene polyurethane, polyvinyl acetate, polyvinyl chloride, polyhydroxybutyrate, polyhydroxyvalerate, ethylene vinyl acetate copolymers, styrene-butadienestyrene copolymers, styrene-isoprene-styrene copolymers, and polylactic acid, polyglycolic acid and copolymers thereof, and mixtures thereof.

* * * * *